United States Patent [19]
Heffelfinger et al.

[11] Patent Number: 5,891,314
[45] Date of Patent: Apr. 6, 1999

[54] METHOD AND APPARATUS FOR CORRECTING LENS NON-UNIFORMITIES IN AN ELECTROPHORESIS APPARATUS

[75] Inventors: David M. Heffelfinger, San Pablo; Craig Van Horn, Sebastapol, both of Calif.

[73] Assignee: Bio-Rad Laboratories, Inc., Hercules, Calif.

[21] Appl. No.: 814,812

[22] Filed: Mar. 10, 1997

[51] Int. Cl.$^6$ ............................ G01N 27/26; G01N 21/00
[52] U.S. Cl. ........................ 204/461; 204/452; 204/612; 204/603; 356/306; 356/344
[58] Field of Search .................................. 204/450, 451, 204/452, 456, 461, 606, 612, 603; 356/306, 344

[56] References Cited

U.S. PATENT DOCUMENTS 5,672,881  9/1997  Striepeke et al. .................... 204/461.2

*Primary Examiner*—Robert Warden
*Assistant Examiner*—Alex Noguerda
*Attorney, Agent, or Firm*— David G. Beck; Townsend & Townsend and Crew

[57] ABSTRACT

A method and apparatus for correcting non-uniformities in the lens assembly of an electrophoresis apparatus is provided. Assuming a detector with a uniform responsivity as well as a uniform illumination source, correcting for lens non-uniformities allows accurate quantitative measurements of an electrophoresis gel to be made, thus increasing the information which can be obtained from an electrophoretic analysis. Applying the system, the non-uniformities due to the lens assembly are first characterized for a range of aperture and magnification settings. A look-up table is then created which contains the non-uniformities and/or correction data files for the lens assembly according to the aperture and magnification settings. In order to correct a sample image, the aperture and magnification settings used to obtain the sample image are provided to the system processor. These settings may be automatically obtained by the processor or manually input by the user. After the processor receives the lens settings, it applies the look-up table to determine the corresponding lens non-uniformities as well as the necessary correction file. The sample image is then normalized by dividing the sample image file by the appropriate correction file. Once normalized, the corrected sample image file may either be displayed or stored for later use.

12 Claims, 6 Drawing Sheets

METHOD AND APPARATUS FOR CORRECTING LENS NON-UNIFORMITIES IN AN ELECTROPHORESIS APPARATUS

The present invention relates generally to electrophoresis reading systems and, more particularly, to a method and apparatus for removing non-uniformities due to the lens assembly in an electrophoresis system.

BACKGROUND OF THE INVENTION

In the biotechnical field, fluorescent dyes are routinely used as sensitive, non-isotopic labels. These labels are used to identify and locate a variety of cell structures, ranging from malignant tumors to specific chromosomes in a DNA sequence. A variety of devices have been designed to read fluorescent-labeled samples.

Gel electrophoresis is one technique commonly used in conjunction with fluorescent dyes and other markers to identify specific molecules as well as other tagged units. In this technique an electric field is used to cause the migration of the tagged units through a gel or other solution.

In U.S. Pat. No. 4,874,492 a gel electrophoresis system is disclosed in which samples are treated with fluorescent markers prior to applying them to an electrophoretic gel. The gel is illuminated with a UV source and the fluorescence pattern is detected with a cooled charge-coupled-device (CCD) two-dimensional detector array. The CCD array is cooled to at least −25 degrees C. in order to improve light sensitivity and increase the dynamic range.

In U.S. Pat. No. 5,162,654 a system is disclosed to optically determine which of four fluorophores is fluorescing in an electrophoresis gel. Fluorescence emitted by the gel passes first through four separate band pass filters and then through four wedge prisms. As a result of this optical configuration, the emitted fluorescence is imaged on four discrete areas on the detector array. The specific fluorophore excited by the irradiation source is determined by comparing the relative intensities of the fluorescence detected in the four detection areas.

In U.S. Pat. No. 5,294,323 the disclosed gel electrophoresis system utilizes a vertical electrophoresis plate. A laser beam passes horizontally through the gel in a direction perpendicular to the longitudinal axis of the electrophoresis plate. The emitted fluorescence is reflected to a solid state imaging sensor such that the reflected pattern is parallel to the direction of the laser beam.

In U.S. Pat. No. 5,324,401 a fluorescence detection system for capillary electrophoresis is disclosed which provides for the simultaneous excitation and detection of fluorescent probes within a plurality of capillaries. The excitation source is a laser which is coupled to the capillaries through an optical fiber bundle. The fluorescence from the capillary array is focussed through a lens and imaged onto a CCD camera for analysis.

In a paper by Sutherland et al. entitled "Electronic Imaging System for Direct and Rapid Quantitation of Fluorescence from Electrophoretic Gels: Application to Ethidium Bromide-Stained DNA" published in *Analytical Biochemistry* 163, 446–457 (1987), the authors describe an imaging system which uses a CCD camera. The CCD camera quantifies the fluorescence received from electrophoretic gels, chromatograms, and other sources. The paper describes several sources of non-uniformities which impact the ability of the system to obtain accurate results.

From the foregoing, it is apparent that an improved electrophoresis apparatus is desired which enables accurate quantitative fluorescence measurements.

SUMMARY OF THE INVENTION

The present invention provides a method and apparatus for correcting for the non-uniformities in an electrophoresis apparatus. These non-uniformities arise from the imaging system. By correcting for these non-uniformities it is possible to make quantitative measurements of an electrophoresis gel, thus increasing the information which can be obtained from the electrophoretic analysis.

The system of the invention uses a look-up table to correct a sample image of any non-uniformities arising from the lens assembly. The look-up table contains the uniformity profiles for the lens assembly for a range of aperture and magnification settings.

In order to correct a sample image, the aperture and magnification settings used to obtain the sample image are provided to a system processor. These settings may be automatically obtained by the processor or manually input by the user. After the processor receives the lens settings, the look-up table is used to determine the corresponding lens non-uniformities. Preferably the look-up table contains a correction file for each pair of lens settings. The sample image is normalized by dividing the sample image file by the appropriate correction file. Once normalized, the corrected sample image file may either be displayed or stored for later use.

A further understanding of the nature and advantages of the present invention may be realized by reference to the remaining portions of the specification and the drawings.

DESCRIPTION OF THE PREFERRED EMBODIMENT

Figure 1:
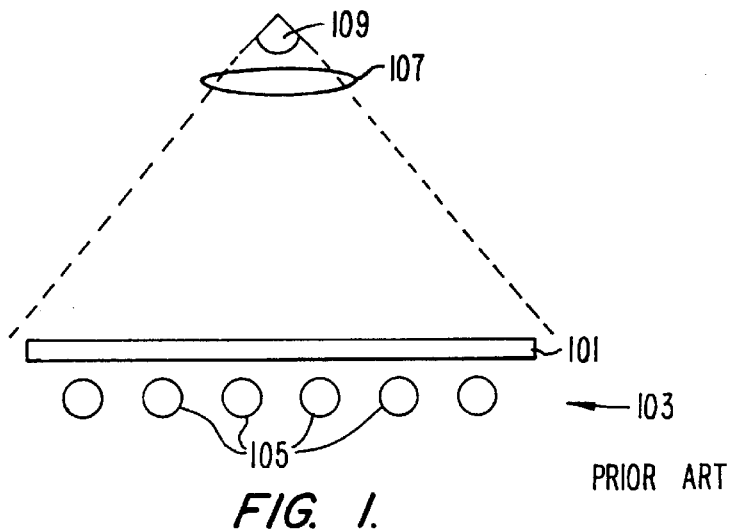
FIG. 1 is an illustration of a cross-section of a gel electrophoresis apparatus according to the prior art.

FIG. 1 is an illustration of a cross-section of a gel electrophoresis apparatus according to the prior art. In this system a gel plate 101 is illuminated by a light source 103. Light source 103 is comprised of a plurality of individual light bulbs 105. The light from source 103 causes fluorophores or other fluorescing material contained within specific areas of sample 101 to fluoresce. The emitted fluorescence passes through one or more lenses 107 and is imaged onto a detector 109. Based upon the received image it is possible to determine the areas of fluorescence on sample 101.

Although the intensity of the fluorescence from sample 101 contains additional information such as the quantity of the fluorescing material, to date the ability to quantify this information has been limited due to non-uniformities in the illumination source, the imaging optics, and the detector. Although the present invention may be used to overcome the non-uniformities associated with the lens assembly, non-uniformities associated with the detector and the illumination source may still prevent a sample from being accurately quantified.

The detector non-uniformities are most easily removed. For example, many CCD arrays are available which offer a linear response over a wide range of intensity levels. Typically these arrays also offer a very uniform response from pixel to pixel, thus dramatically reducing any non-uniformities arising from the detector.

The light intensity from an individual light bulb 105 is relatively uniform along the majority of the length of the bulb. At either end of the bulb the brightness level exhibits a minor fall-off in intensity. This fall-off can be minimized through the use of reflectors, masks, diffusion filters, or some combination thereof. The effects of fall-off can also be minimized by simply using longer bulbs. By extending the bulbs, the end portions of the bulbs exhibiting the lower brightness levels are located past the sampling area of the apparatus, thus placing only the relatively uniform length of the bulb under the sample.

Figure 2:
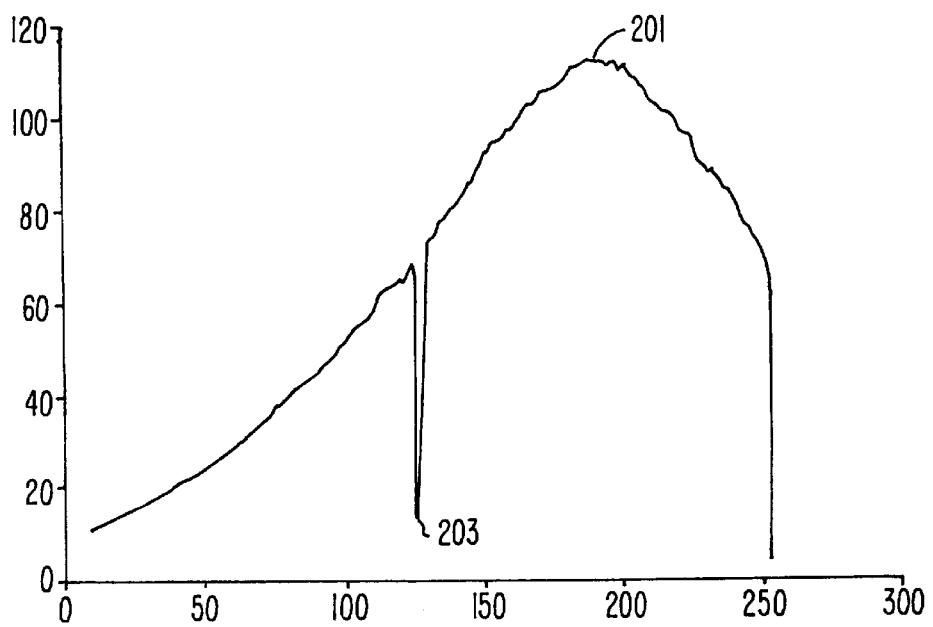
FIG. 2 is the intensity profile of a single light bulb measured perpendicular to the axis of the bulb.
Figure 3:
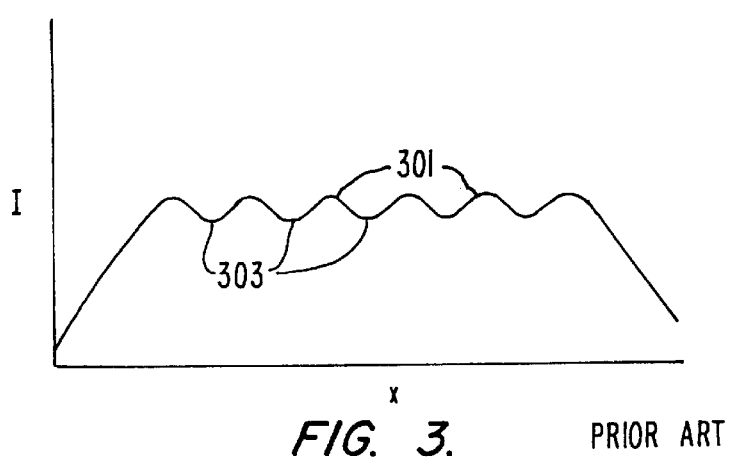
FIG. 3 is an illustration of an intensity profile for a source with multiple bulbs.

FIG. 2 is the intensity profile of a single light bulb 105 measured perpendicular to the axis of the bulb. As expected, the profile exhibits a peak 201 centered directly above the bulb with a rapid fall off in the intensity as the distance from the bulb is increased. A dip 203 is a result of a scribe mark on the stage. FIG. 3 is an illustration of an intensity profile for source 103 measured perpendicular to the axes of bulbs 105. Peaks 301 are located over the center lines of the individual bulbs 105 while valleys 303 represent the midpoints between bulbs. Further improvement in source uniformity can be achieved by increasing the number of bulbs and decreasing the separation between bulbs.

Figure 4:
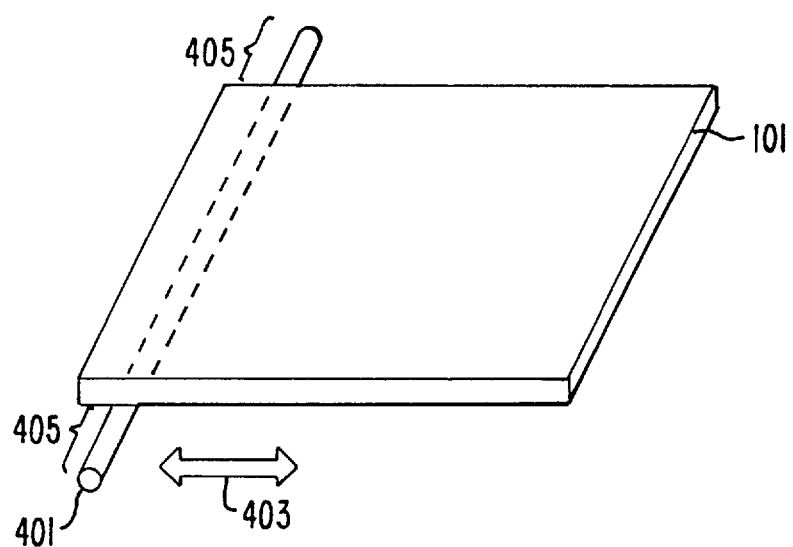
FIG. 4 is an illustration of a method of improving the uniformity of an illumination source.

FIG. 4 is an illustration of another method of improving the uniformity of the illumination source. In this method sample 101 is illuminated with a single source 401. Although source 401, as shown, is comprised of a single bulb, source 401 may also be comprised of multiple bulbs. Source 401 is scanned in a direction 403 perpendicular to the axis of the bulb, thus taking advantage of the high degree of intensity uniformity along the central bulb portion. The effects of intensity fall-off near either end of the bulb may be minimized by extending the bulb past the edges of sample 101 by a distance 405. Since source 401 is scanned in a direction perpendicular to the region of bulb uniformity, sample 101 will be uniformly illuminated as long as the scanning rate remains constant.

Figure 5:
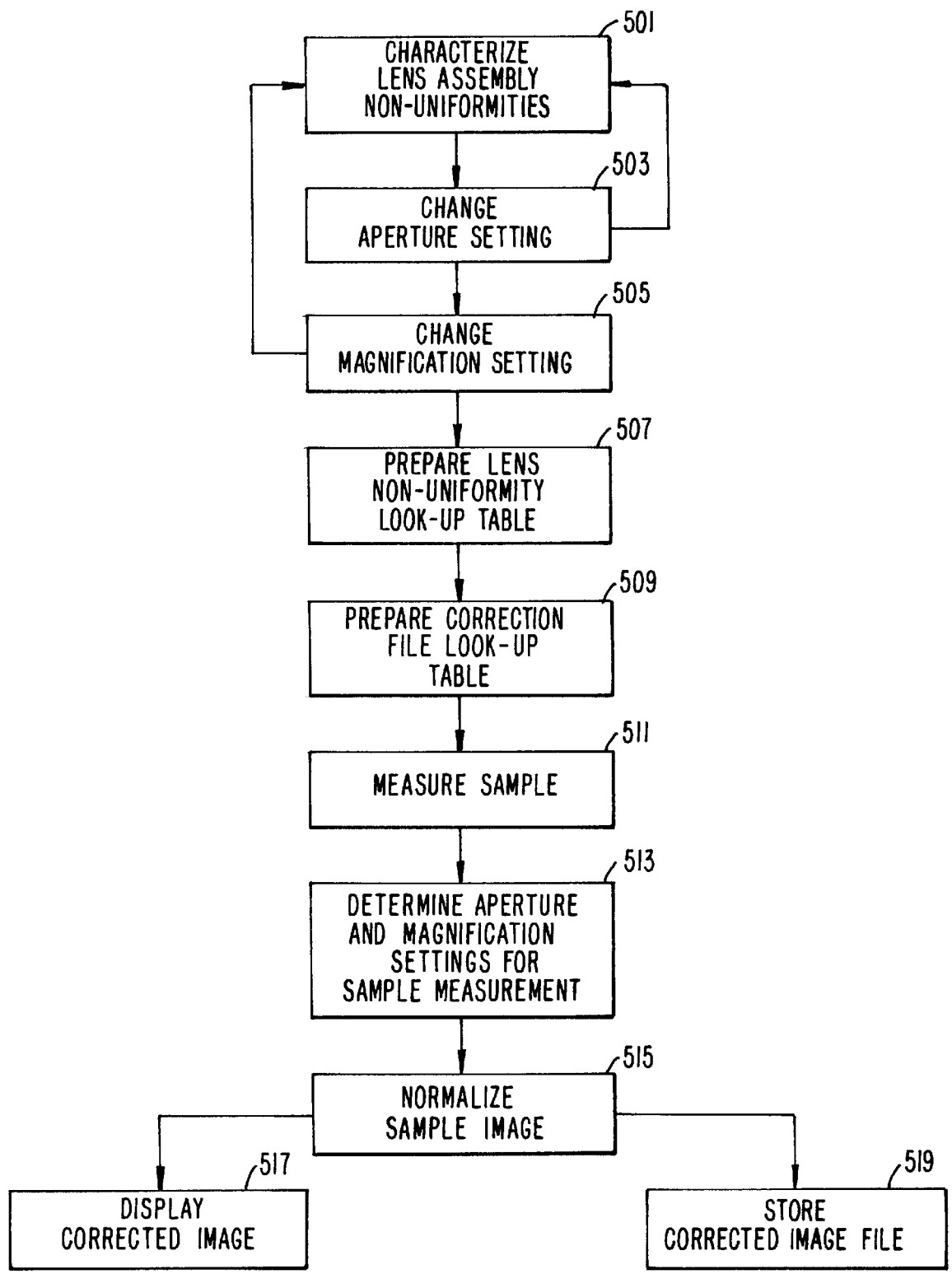
FIG. 5 is a block diagram outlining the principal steps in correcting an image for lens non-uniformities based on the present invention.

FIG. 5 is a block diagram outlining the principal steps in correcting an image for lens non-uniformities based on the present invention. First, the non-uniformities of the lens assembly are measured (step 501). A number of techniques can be used to determine lens non-uniformities, a few of which are described below. After the lens assembly has been characterized for an initial set of aperture and magnification settings, these settings are changed (steps 503 and 505) and the lens is recharacterized. This process continues until the lens assembly has been characterized for a range of aperture settings and a range of magnification settings. This information is then used to create a look-up table or matrix (step 507).

After the lens characterization look-up table has been created, this data is converted to a correction file look-up table (step 509). This step may be required in order to create a one to one correspondence between the number of correction data points per correction file and the number of data points resulting from the sample imaging process. Depending upon the technique used to characterize the lens assembly, the number of correction data points may be substantially less than the number of sample points. In this case the additional correction data points are filled-in by the data processor using well known interpolation techniques and taking advantage of any symmetry of the lens assembly.

After a look-up table of correction files has been created, the system is used to image an electrophoresis sample gel (step 511). At this time the user may either view the uncorrected sample image or store a sample file of the uncorrected image for correction and later viewing. Prior to correcting the sample image, the aperture and magnification settings used to obtain the sample image must first be determined (step 513) since this data is required in order to locate the appropriate correction file within the correction file look-up table. This information can either be determined automatically by the system or the user can simply input the lens settings.

To remove the lens assembly non-uniformities from the sample image, the sample file is normalized by dividing it by the appropriate correction file (step 515). Prior to normalization, the correction files may first be smoothed using a smoothing function such as those well known in the art. The smoothing function insures that any source of noise in the correction file is not amplified by the normalization process. Lastly, the corrected sample image is either displayed (step 517) or stored (step 519) for future use.

Figure 6:
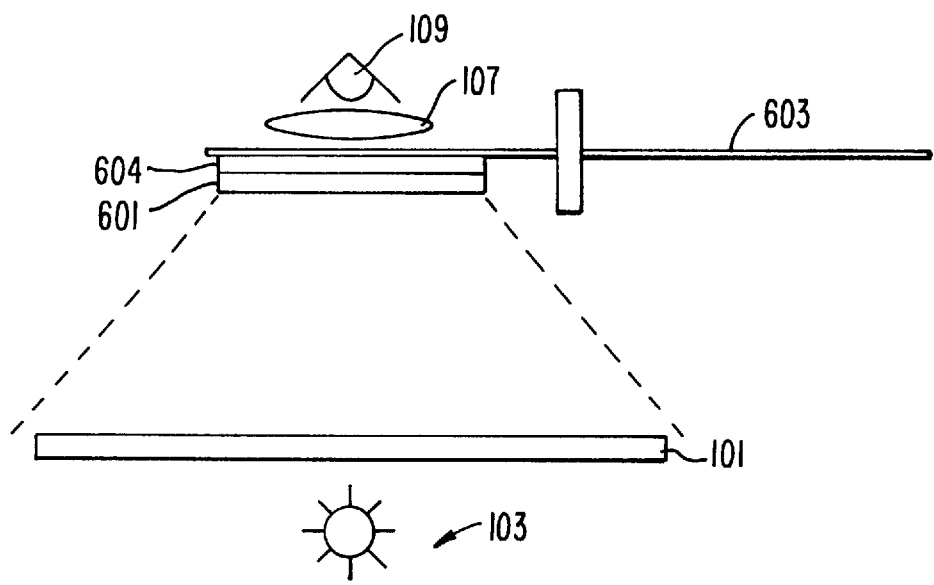
FIG. 6 is an illustration of one method of determining the non-uniformities of the lens assembly.

FIG. 6 is an illustration of one method of determining the non-uniformities of the lens assembly. As in the system illustrated in FIG. 1, fluorescence from a sample 101 is imaged onto a detector 109 by a lens 107. In order to characterize the lens assembly, a calibration standard 601 is moved into place with a stage 603. Calibration standard 601 is a piece of fluorescent glass or plastic which uniformly fluoresces when illuminated with a suitable source. Preferably calibration standard 601 fluoresces at the same wavelength as the fluorescent labels used with the sample, thus insuring that the standard accurately reproduces the non-uniformities of the lens assembly. Optionally, a diffuser 604 may be mounted between calibration standard 601 and lens 107. Diffuser 604 insures that the system only monitors the non-uniformities of the lens and detector by smoothing out even the small non-uniformities within the calibration standard.

Preferably standard 601 is placed in close proximity to the entrance aperture of lens 107 and stage 603 is a rotation stage. In order to obtain an accurate mapping of the non-uniformities of the lens, calibration standard 601 must completely fill the aperture of the lens.

Figure 7:
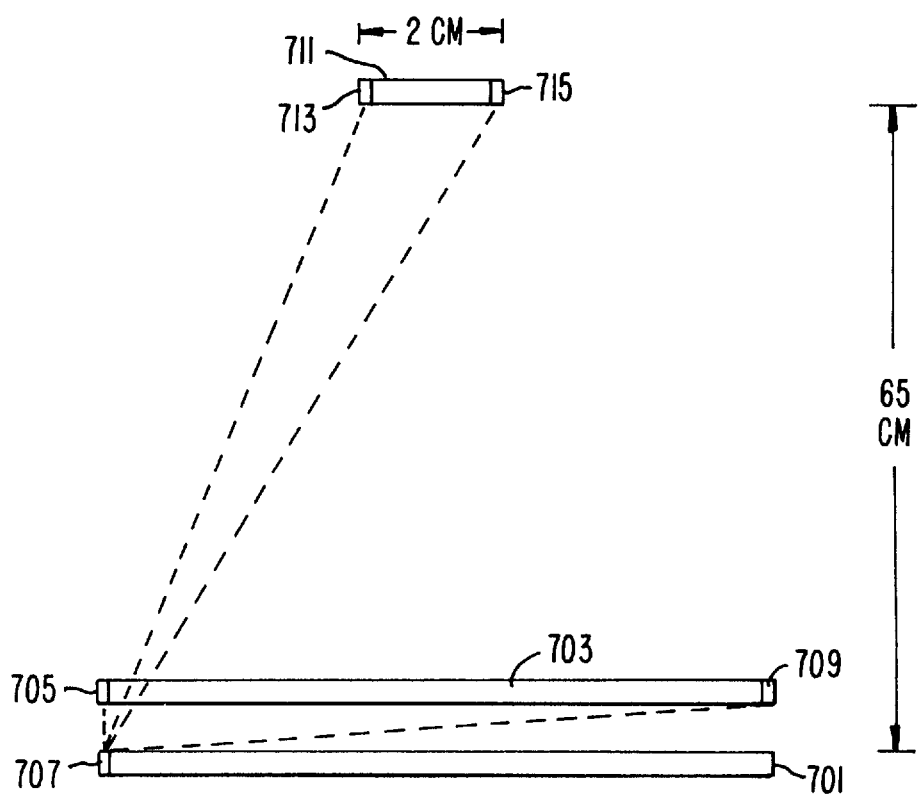
FIG. 7 illustrates the relationship between light uniformity and the calibration standard used in one characterization technique.

Light uniformity is not required during the lens characterization step using this calibration technique given the distance separating light source 103 from standard 601. FIG. 7 illustrates the relationship between light uniformity and the placement of the calibration standard. A light source 701 illuminates a calibration standard 703 placed in close proximity to light source 701. As defined by Lambert's Law, the intensity of a small incremental area of the source, $J_\theta$, is equivalent to the intensity of the incremental area in the direction of the normal, $J_0$, times the cosine of the angle $\theta$ as measured from the surface normal. Therefore the intensity measured at a point 705 on standard 703 which is directly above an area 707 of source 701 is equivalent to the intensity of area 707. In contrast, the intensity measured at a point 709 at the opposite end of standard 703 is significantly reduced. For example given an angle $\theta$ of 80 degrees, the intensity at point 709 is only 17percent of the intensity measured at point 705. Thus if source 701 is non-uniform, calibration standard 703 will be non-uniformly illuminated, resulting in a calibration technique which is a function not only of lens and detector non-uniformities, but also a function of illumination non-uniformities.

In contrast, if a calibration standard is used which is located at some distance from source 701, the illumination non-uniformities have little impact on the calibration technique. For example, assuming that a calibration standard 711 measuring 2 centimeters in diameter is located 65 centimeters from source 701, there is less than 1 percent difference in intensity as measured at points 713 and 715. Thus by placing the calibration standard near the lens and at a distance from the source, the effects of illumination non-uniformities can be greatly minimized.

Figure 8:
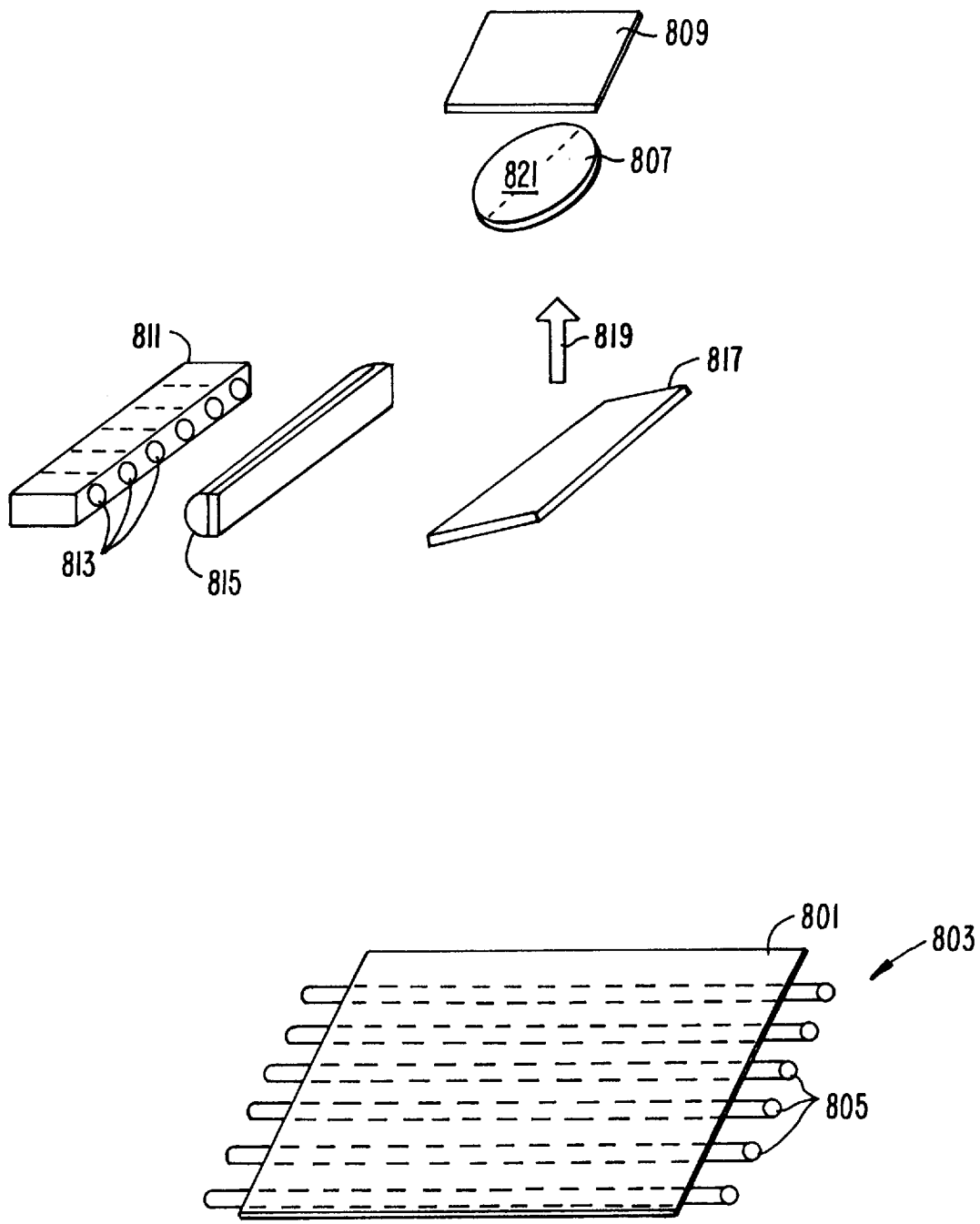
FIG. 8 is an illustration of another method of determining the non-uniformities of the lens assembly.

FIG. 8 is an illustration of another method of determining the non-uniformities of the lens assembly. A sample plane 801 is illuminated with a light source 803. In this embodiment light source 803 consists of a series of light bulbs 805 although this technique is equally applicable to other light sources. In normal usage a sample, for example an electrophoresis gel, would lie within sample plane 801. The fluorescence from the excited regions of such a sample would be imaged by a lens assembly 807 onto a detector 809.

In order to characterize the lens assembly 807, a secondary source 811 is used. Source 811 is a line source, for example a series of light emitting diodes (LEDs) 813. Source 811 may also consist of a series of other types of point sources or a single line source such as a long light bulb. The radiation from source 811 is enlarged with a lens 815 before being reflected by a mirror 817. Mirror 817 may be a partial reflector thus allowing it to remain in place during the normal operation of the system. Mirror 817 may also be dedicated to the task of measuring the lens non-uniformities. If mirror 817 is a dedicated mirror, it is placed on a stage so that it can be moved out of the sample imaging path during normal system operation.

Mirror 817 reflects the radiation from source 811 along a path 819. The radiation then passes through lens assembly 807 onto detector 809. Assuming a uniform detector response (e.g., sensitivity) as is obtainable with a CCD array, and also assuming uniformity in mirror 817, lens 815, and source 811, any non-uniformity measured by detector 809 is due to lens assembly 807.

The apparatus illustrated in FIG. 8 assumes that lens assembly 807 exhibits a spherical symmetry, thus allowing the lens non-uniformities to only be determined along a single axis 821. If lens assembly 807 does not exhibit such symmetry, additional non-uniformity measurements must be made along other axes.

Figure 9:
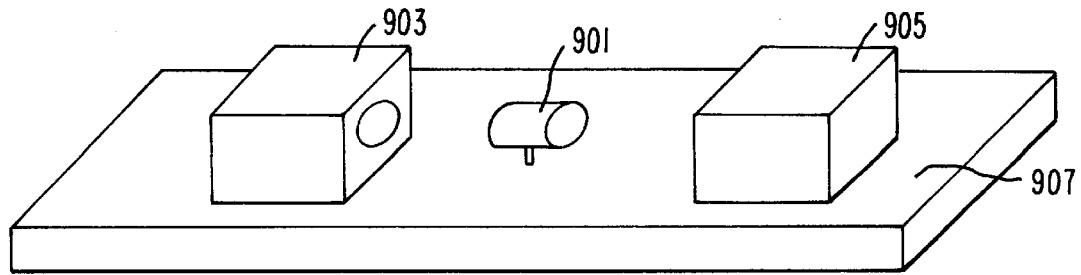
FIG. 9 is an illustration of another method of determining the non-uniformities of the lens assembly.

Another method of characterizing the lens assembly non-uniformities is to remove the lens assembly and characterize it separately from the electrophoresis apparatus. For example in the system illustrated in FIG. 9, a lens assembly 901 is removed from an electrophoresis apparatus (not shown) and placed between a source 903 and a detector 905 on a calibration bench 907. Given this environment, an extremely uniform source 903 and detector 905 may be used thus insuring a high degree of characterization accuracy. Once characterized, lens assembly 901 is refitted to the electrophoresis apparatus.

Figure 10:
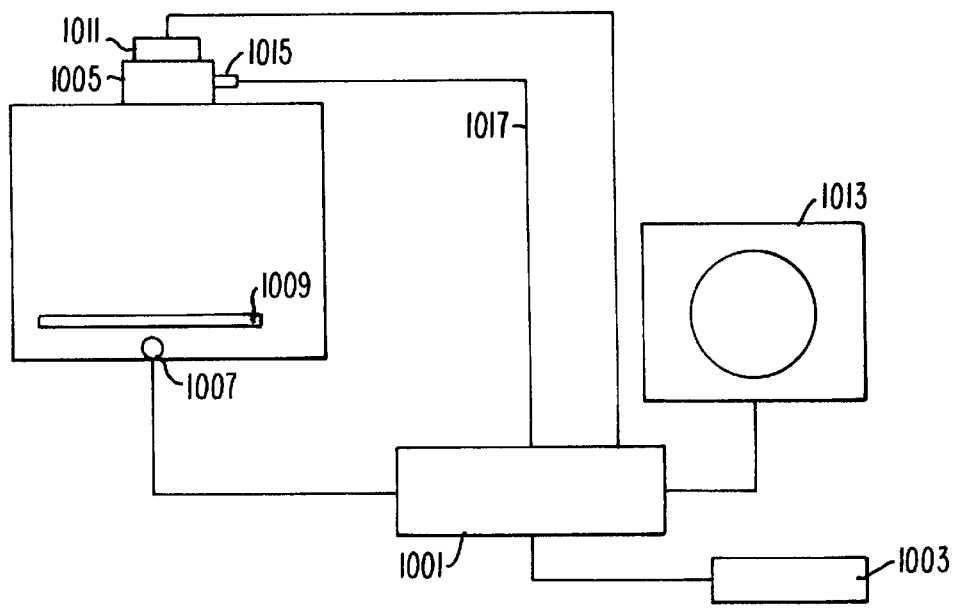
FIG. 10 is an illustration of the major components of a system according to the present invention.

FIG. 10 is an illustration of the major components of a system according to the present invention. In this embodiment the key system components are coupled to a processor 1001 which is coupled to a user interface 1003. Processor 1001 is required for the interpolation and normalization processes to be performed in a timely fashion. This embodiment can be used regardless of the method used to characterize the non-uniformities of lens assembly 1005.

To take a sample image, a source 1007 is turned on causing the appropriately marked regions of sample 1009 to fluoresce. The fluorescence is imaged by lens assembly 1005 onto a detector 1011. The sample image may either be displayed immediately on a display monitor 1013 or stored as a sample file within a memory associated with processor 1001.

In order to correct the sample image for lens non-uniformities, the lens aperture and magnification settings used during the acquisition of the sample image must be input into processor 1001. These settings are required in order to allow processor 1001 to determine the appropriate correction file to be used during the normalization process. After the image file is normalized using the appropriate correction file, a corrected image file can be displayed on monitor 1013. A corrected image file can also be stored within memory for later retrieval and use.

There are a number of different ways in which the lens settings may be obtained by processor 1001. The most straightforward method is for the user to manually input the setting information using interface 1003. In a second method, the lens settings are automatically determined by processor 1001. In this embodiment lens 1005 contains one or more setting sensors 1015. Sensors 1015 are coupled to processor 1001 by a line 1017. Sensors 1015 are either mechanical or electro-optical, employing well known technologies.

Figure 11:
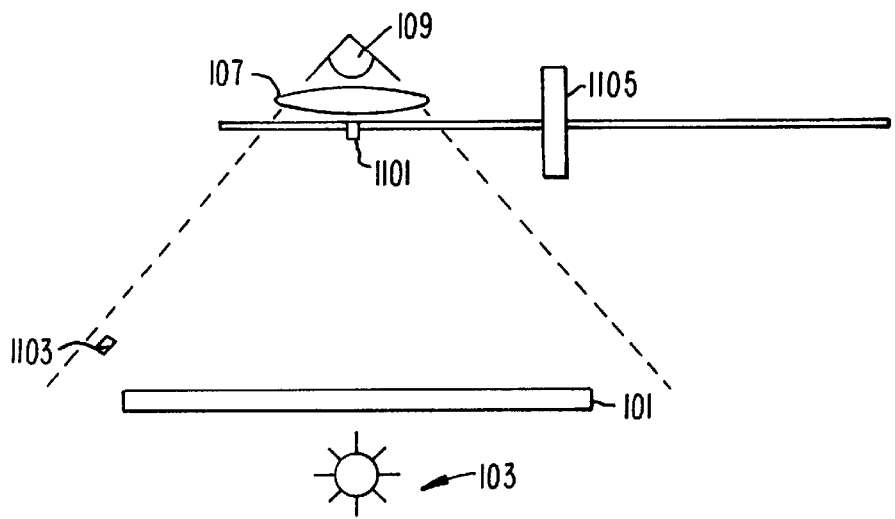
FIG. 11 is an illustration of a method used to determine the aperture and magnification settings of a lens assembly.

FIG. 11 is an illustration of another technique utilizing a single calibrated light source to determine the aperture and magnification settings of lens 107. The light source can be a light emitting diode (LED) or other form of easily calibrated source. The source can be located at a position 1101 or at a stationary, out-of-field position, 1103. If the source is placed within the field-of-view of the imager, such as location 1101, it must be removable. For example, a stage 1105 can be used to move the source into position.

In order to use this method to determine the lens settings, the calibrated source is placed into position and turned on. An image is taken of the source using the same settings as were used to take an image of the sample in question. The magnification setting is determined by looking at the image size of the calibrated source while the aperture setting is determined by the intensity of the source.

As will be understood by those familiar with the art, the present invention may be embodied in other specific forms without departing from the spirit or essential characteristics thereof. For example, other techniques of characterizing the lens non-uniformities may be used. Accordingly, the disclosures and descriptions herein are intended to be illustrative, but not limiting, of the scope of the invention which is set forth in the following claims.

We claim:

1. An apparatus for obtaining a corrected image of an electrophoresis gel, said electrophoresis gel illuminated by a light source, comprising:

a lens assembly set at a first aperture setting and a first magnification setting, said lens assembly imaging said illuminated electrophoresis gel onto a detector, wherein said detector generates an output signal corresponding to said image of said electrophoresis gel, and wherein said lens assembly is capable of a plurality of aperture settings and a plurality of magnification settings;

a processor coupled to said detector;

an input source coupled to said processor, wherein said input source inputs said first aperture setting and said first magnification setting into said processor;

a look-up table coupled to said processor, said look-up table containing a plurality of lens assembly non-uniformity profiles corresponding to said plurality of aperture settings and said plurality of magnification settings, wherein said plurality of lens assembly non-uniformity profiles are stored in said processor as a plurality of correction files; and a corrected image file stored in said processor, wherein said processor generates said corrected image by normalizing said image file with a correction file selected from said look-up table and corresponding to said first aperture setting and said first magnification setting.

2. The apparatus of claim 1, wherein said detector is a CCD detector array.

3. The apparatus of claim 1, further comprising a display monitor coupled to said processor for displaying said corrected image file.

4. The apparatus of claim 1, wherein said input source is a manual input source.

5. The apparatus of claim 1, wherein said input source is further comprised of a lens assembly aperture setting sensor and a lens assembly magnification setting sensor, wherein said aperture setting sensor sends a first sensor signal corresponding to a selected aperture setting to said processor and said magnification setting sensor sends a second sensor signal corresponding to a selected magnification setting to said processor.

6. The apparatus of claim 1, wherein said input source is further comprised of a second light source, wherein said second light source is a calibrated source, wherein said second light source is imaged on said detector by said lens assembly forming a first magnified image of a first intensity, wherein said processor determines said first magnification setting based on a size of said magnified image, and wherein said processor determines said first aperture setting based on said first intensity.

7. The apparatus of claim 1, wherein said light source illuminates said electrophoresis gel with a substantially uniform illumination.

8. A method of removing lens assembly non-uniformities from an image of an electrophoresis gel, the method comprising the steps of:

illuminating said electrophoresis gel with a light source, wherein at least one labeled region of said illuminated gel fluoresces;

selecting a first aperture setting from a plurality of aperture settings for a lens assembly;

selecting a first magnification setting from a plurality of magnification settings for said lens assembly;

imaging said illuminated electrophoresis gel onto a detector with said lens assembly;

outputting a first signal to a processor, said first signal corresponding to said image of said illuminated electrophoresis gel;

storing said first output signal as an image file in a memory coupled to said processor;

communicating said first aperture setting to said processor;

communicating said first magnification setting to said processor;

determining an appropriate correction file from a look-up table containing a plurality of correction files corresponding to said plurality of aperture settings and said plurality of magnification settings, wherein said appropriate correction file corresponds to said first aperture setting and said first magnification setting; and generating a corrected image file by normalizing said image file with said appropriate correction file.

9. The method of claim 8, further comprising the step of storing said corrected image file in said memory.

10. The method of claim 8, further comprising the step of displaying said corrected image file on a display monitor.

11. The method of claim 8, wherein said communicating steps are performed with a user interface coupled to said processor.

12. The method of claim 8, wherein said communicating steps are further comprised of the steps of:

imaging a second source onto said detector, wherein said second source is a calibrated source;

measuring an intensity of said imaged calibrated source;

determining said first aperture setting from said intensity;

measuring a size of said imaged calibrated source; and determining said first magnification setting from said size.

* * * * *